(12) United States Patent
Soden et al.

(10) Patent No.: US 10,953,093 B2
(45) Date of Patent: Mar. 23, 2021

(54) METHOD FOR TREATING CANCER

(71) Applicant: UNIVERSITY COLLEGE CORK, Cork (IE)

(72) Inventors: Declan Soden, Cork (IE); Patrick Forde, Cork (IE); Morgan O'Brien, Cork (IE)

(73) Assignee: University College Cork, Cork (IE)

( * ) Notice: Subject to any disclaimer, the term of this patent is extended or adjusted under 35 U.S.C. 154(b) by 49 days.

(21) Appl. No.: 16/182,015

(22) Filed: Nov. 6, 2018

(65) Prior Publication Data
US 2019/0076528 A1 Mar. 14, 2019

Related U.S. Application Data

(63) Continuation of application No. 15/309,464, filed as application No. PCT/IB2015/053384 on May 8, 2015, now Pat. No. 10,143,750.

(30) Foreign Application Priority Data

May 8, 2014 (GB) ..................... 1408119

(51) Int. Cl.
| | | |
|---|---|---|
| *A61K 41/00* | (2020.01) | |
| *A61K 38/20* | (2006.01) | |
| *A61K 45/06* | (2006.01) | |
| *A61M 37/00* | (2006.01) | |

(52) U.S. Cl.
CPC ...... *A61K 41/0047* (2013.01); *A61K 38/2013* (2013.01); *A61K 45/06* (2013.01); *A61M 37/00* (2013.01); *A61M 2037/0007* (2013.01)

(58) Field of Classification Search
CPC ............ A61K 38/2013; A61K 41/0047; A61K 45/06; A61M 2037/0007; A61M 37/00; A61P 35/00
See application file for complete search history.

(56) References Cited

U.S. PATENT DOCUMENTS 8,709,417 B2 * 4/2014 Allison ............ A61K 39/39558
424/130.1
2003/0018006 A1 1/2003 Tao et al.

FOREIGN PATENT DOCUMENTS

| WO | 2005103086 A1 | 11/2005 |
|---|---|---|
| WO | 2006010838 A2 | 2/2006 |
| WO | 2008137915 A2 | 11/2008 |
| WO | 2011041613 A2 | 4/2011 |
| WO | 2014096275 A1 | 6/2014 |

OTHER PUBLICATIONS

Roux, et al. (2008) "Tumor destruction using electrochemotherapy followed by CpG oligodeoxynucleotide injection induces distant tumor responses", Cancer Immunology and Immunotherapy, 57(9): 1291-300. (Year: 2008).*

(Continued)

*Primary Examiner* — Deanna K Hall
(74) *Attorney, Agent, or Firm* — Studebaker & Brackett PC

(57) ABSTRACT

The present invention relates to a method for the treatment of cancer in a subject which comprises the steps of: (i) administering electroporation to a tumour in the subject; and (II) administering a T or B-cell activating agent to the subject, wherein step (i) and (II) may be performed in either order.

15 Claims, 11 Drawing Sheets

(56) References Cited

OTHER PUBLICATIONS

Fan, et al. (2014)"Engagement of the ICOS pathway markedly enhances efficacy of CTLA-4 blockade in cancer immunotherapy", Journal of Internal Medicine, 211(4): 715-25. (Year: 2014).*

Frandsen et al. (2012) "Direct Therapeutic Applications of Calcium Electroporation to Effectively Induce Tumor Necrosis", Cancer Research, 72(6): 1336-41. (Year: 2012).*

Ariffin et al. (2014) "Releasing Pressure in Tumors: What do we know so far and where do we go from here? A Review", Cancer Research: 74(10) 2655-62. (Year: 2014).*

Ariffin et al., "Releasing pressure in tumors: what do we know so far and where do we go from here?" A review"", Cancer Res., 74(10):2665-62 (2014).

Faget et al., "ICOS-ligand exression on Plasmacytoid dendritic cells supports breat scancer progression by promoting the accumulation of immunosuppressive CD4+ T cells", Cancer Res., 72(23):6130-40 (2012).

Forde at al., "Enhancement of electroporation facilitated immunogen therapy via T-reg depletion", Cancer Gener Ther., 21(8):349-54 (2014).

International Preliminary Report on Patentability, International Application No. PCT/IB2015/053384, dated Nov. 8, 2016.

International Search Report, International Application No. PCT/IB2015/053384, dated Aug. 6, 2015.

Jahangeer et al., "Review of current thermal ablation treatment of lung cancer and the potential of electrochemotherapy as a means of treatment for lung tumours", 39(8): 862-71 (2013).

Mir et al., "Electrochemotherapy tumor treatment is improved by interleukin-2 stimulation of the host's defenses", Eur, Cytokine Netw., 3(#):331-4 (1992).

O'Brien et al., "Local tumour ablative therapies: opportunities for maxsimising immune engagement and activation", Biochim. Biophys. Acta., 1846(2):510-23 (2014).

Roux et al., "Tumor destruction using electrochemotherapy followed by CpG oligodeoxynucleotide injection induces distant tumor response", Cancer Immunol. Immunother., 57(9):1291-300 (2008).

McDonald et al., (2008) "A phase I clinical study of VB4*845: Weekly intratumoral administration of an anti-EpCAM recombinant fusion protein in pateints with squamous cell carcinoma of the head and nexk", Drug Design, Development Therapy, 2: 105-14.

Fan et al., (2014) "Engagement of the ICOS pathway markedly enhanves afficacy of CTLA-4 blockade in cancer immunotherapy", JOurnal of Internal Medicine, 211(4): 715-25.

* cited by examiner

METHOD FOR TREATING CANCER

FIELD OF THE INVENTION

The present invention relates to a method for treating cancer in a subject.

BACKGROUND TO THE INVENTION

Electrochemotherapy (ECT) is a local treatment of cancer, which combines the use of a medical device with pharmaceutical agents to achieve local tumour control in solid cancers. The procedure consists of applying short high-intensity pulsed electric fields to cells, in response to which the plasma membrane's permeability to various molecules transiently increases. This facilitates cellular uptake of cytotoxic agents, thus increasing their cytotoxicity. The treatment is based on electroporation, which occurs when an externally delivered electric field induces a sufficiently large transmembrane voltage. Electroporation is, in addition to its use in electrochemotherapy, used also as non-viral gene delivery method to cells in vitro and in vivo—gene electrotransfer. Furthermore, electroporation as sole modality can be used as tumour ablation in the form of irreversible electroporation, also referred to as non-thermal irreversible electroporation.

Applications for electrochemotherapeutic-based treatment of cutaneous and subcutaneous tumours using drugs such as bleomycin and cisplatin have reached clinical use. ECT with bleomycin was used to treat a patient for the first time in 1991, while ECT with cisplatin was used for the first time in 1995. Multiple positioning of the electrodes, and subsequent pulse delivery, can be performed during a session to treat the whole lesion, provided that drug concentration is sufficient. Treatment can be repeated over the course of weeks or months to achieve regression of large lesions.

In a number of clinical studies (phase II and phase III), investigators have concluded that ECT of cutaneous or subcutaneous metastasis or tumours with bleomycin and cisplatin have an objective response rate of more than 80%. Reduction of tumour size has been achieved with electrochemotherapy faster and more efficiently than in standard chemotherapy for both cutaneous and subcutaneous tumours.

Whilst studies have shown that ECT is effective at achieving local tumour reduction and potential tumour resolution, it is largely incapable of generating a systemic antigen specific T/B cell immune response. This incapability can lead to disease reoccurrence.

There is thus a need for a cancer therapy, which is not associated with these issues.

Representative CT26 tumor growth curve. Each Balb/C mouse was subcutaneously injected with $1 \times 10^6$ CT26 cells in the flank. When tumours reached an approximate size of 100 mm³ they were treated with electroporation only (■), electrochemotherapy only (▲), electrochemotherapy combined with ICOS (●) or untreated (●). 6 mice/groups were used and the experiment was performed twice. Tumour volume was calculated using the formula $V = ab^2\pi/6$. Data is presented as the means±standard error of the mean.

Figure 2:
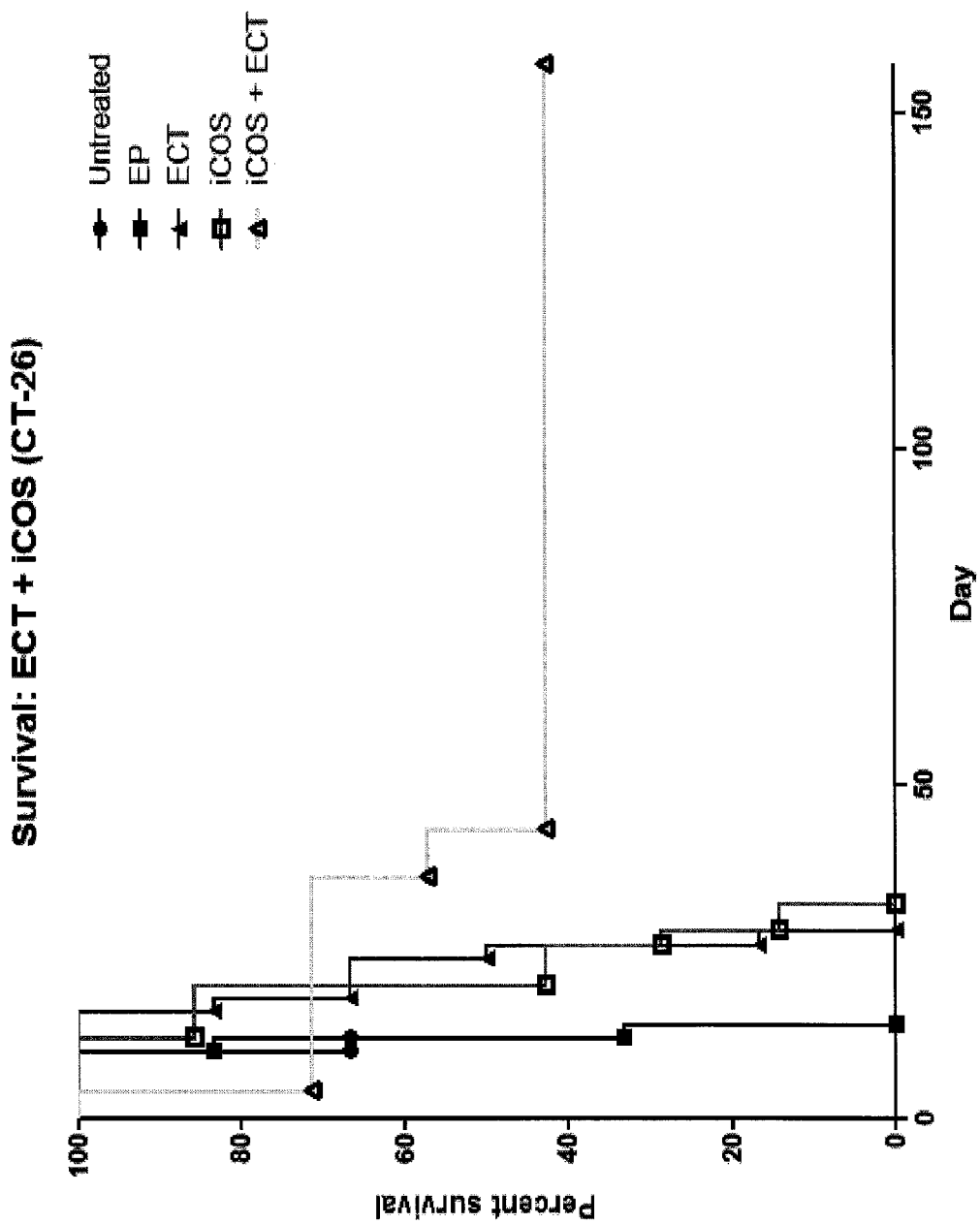

FIG. 2: Kaplan-Meier survival curve ECT combined with ICOS in CT26 model

Representative Kaplan-Meier survival curve of CT26 treated tumours was measured. Only mice treated with ICOS/ECT combination survived. 40% of mice survived and were still alive at approx. 200 days. All other groups were sacrificed by day 38.

Figure 3:
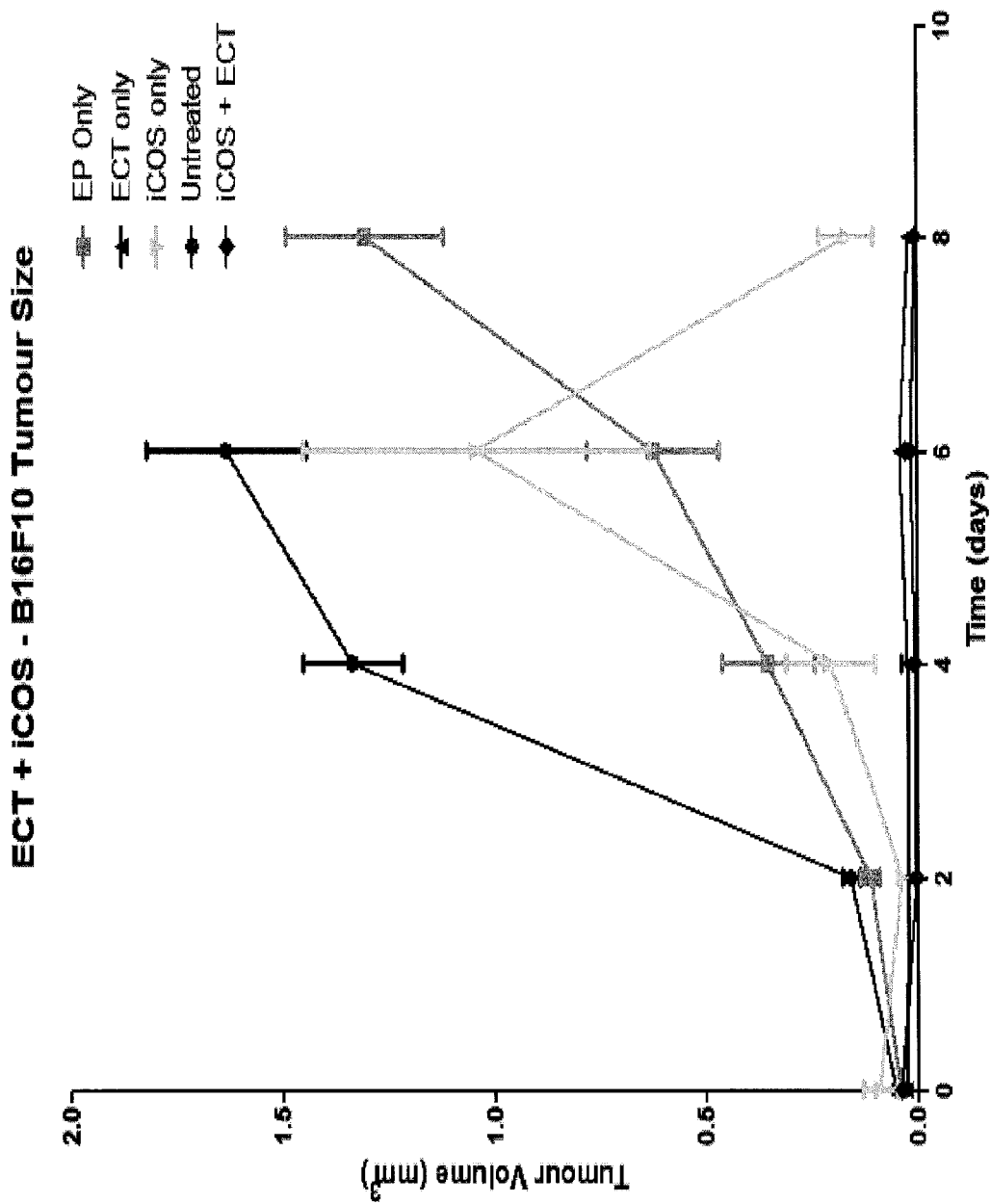

FIG. 3: Growth curve of ECT combined with ICOS in B16F10 model

Representative growth curve of B16F10 tumour. Each C57BL/6J was subcutaneously injected with $2 \times 10^5$ B16F10 cells in the flank of the mice. When the tumours grew to an approximate size of 100 mm³ they were treated with electroporation only (■), electrochemotherapy only (▲), electrochemotherapy combined with ICOS (♦) ICOS only (▼) or untreated (●). 6 mice/groups were used and the experiment was performed twice. Tumor volume was calculated using the formula $V=ab^2\pi/6$. Data is presented as the means±standard error of the mean.

Figure 4:
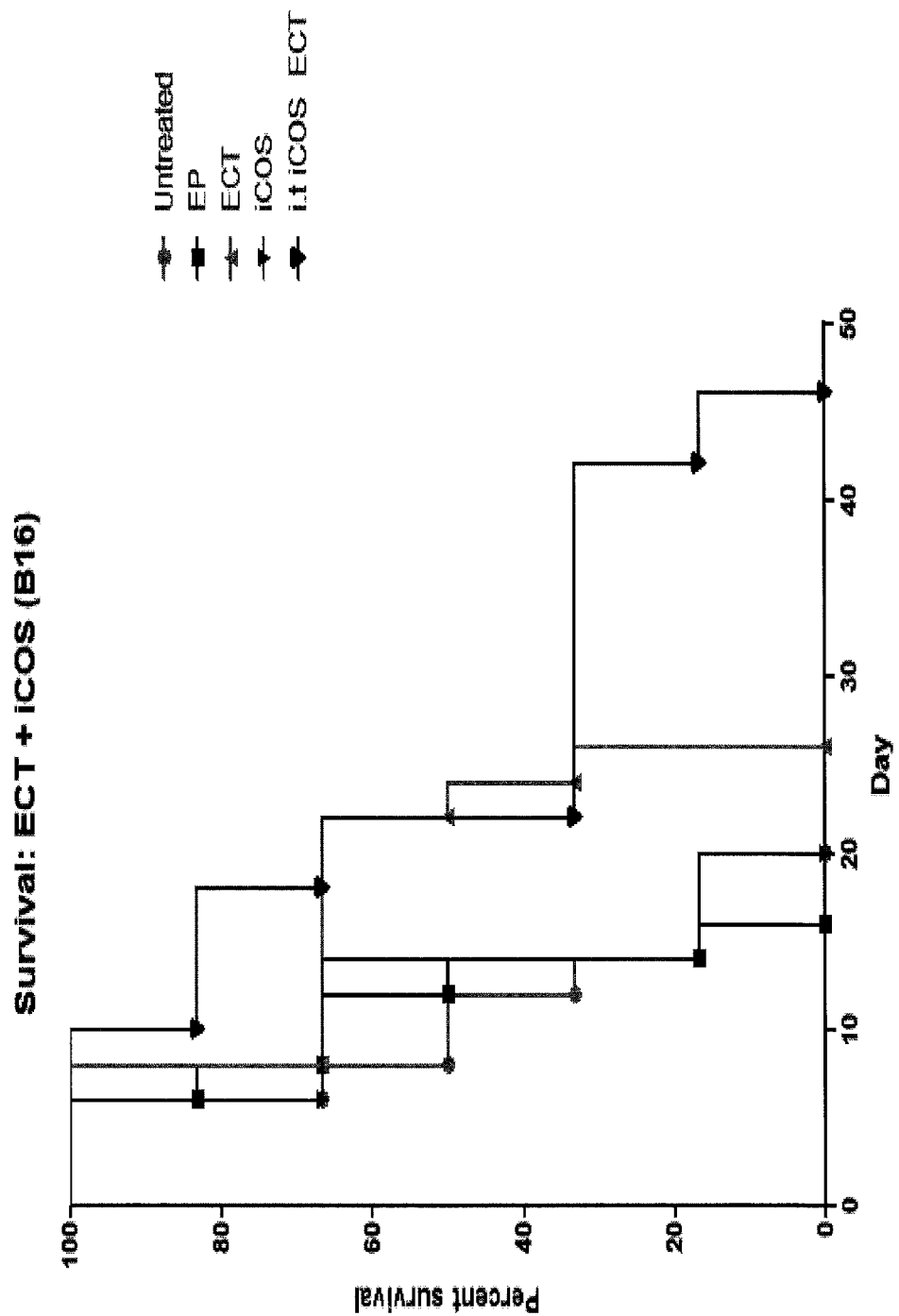

FIG. 4: Kaplan-Meier survival curve ECT combined with ICOS in B16F10 model

Representative Kaplan-Meier survival curve of B16F10 treated tumours was measured. Mice treated with ICOS/ECT combination survived to 48 days. All other groups were sacrificed by day 25.

Figure 5:
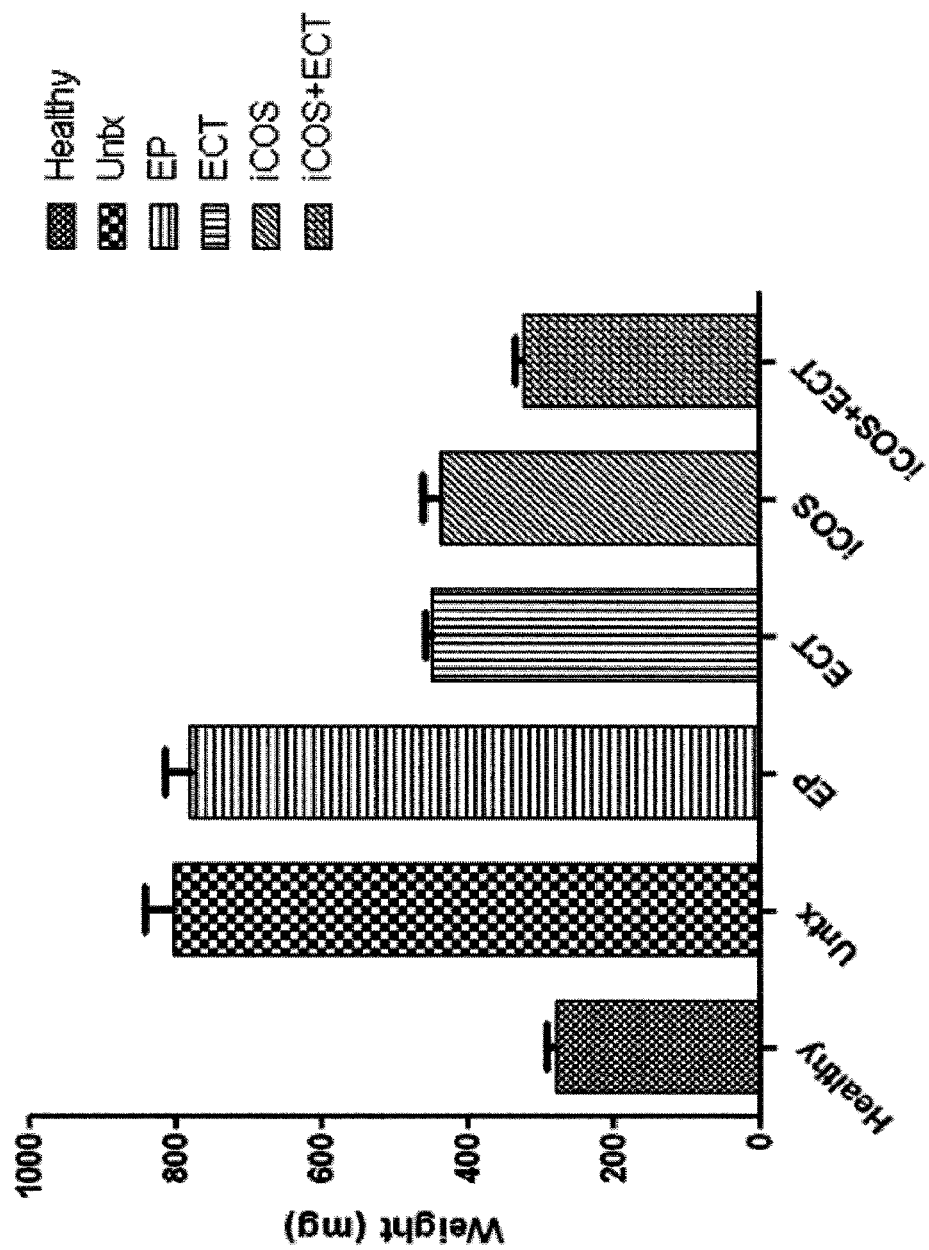

FIG. 5: Lung metastases burden

Measured lung weight in lung metastatic cancer model.

Figure 6:
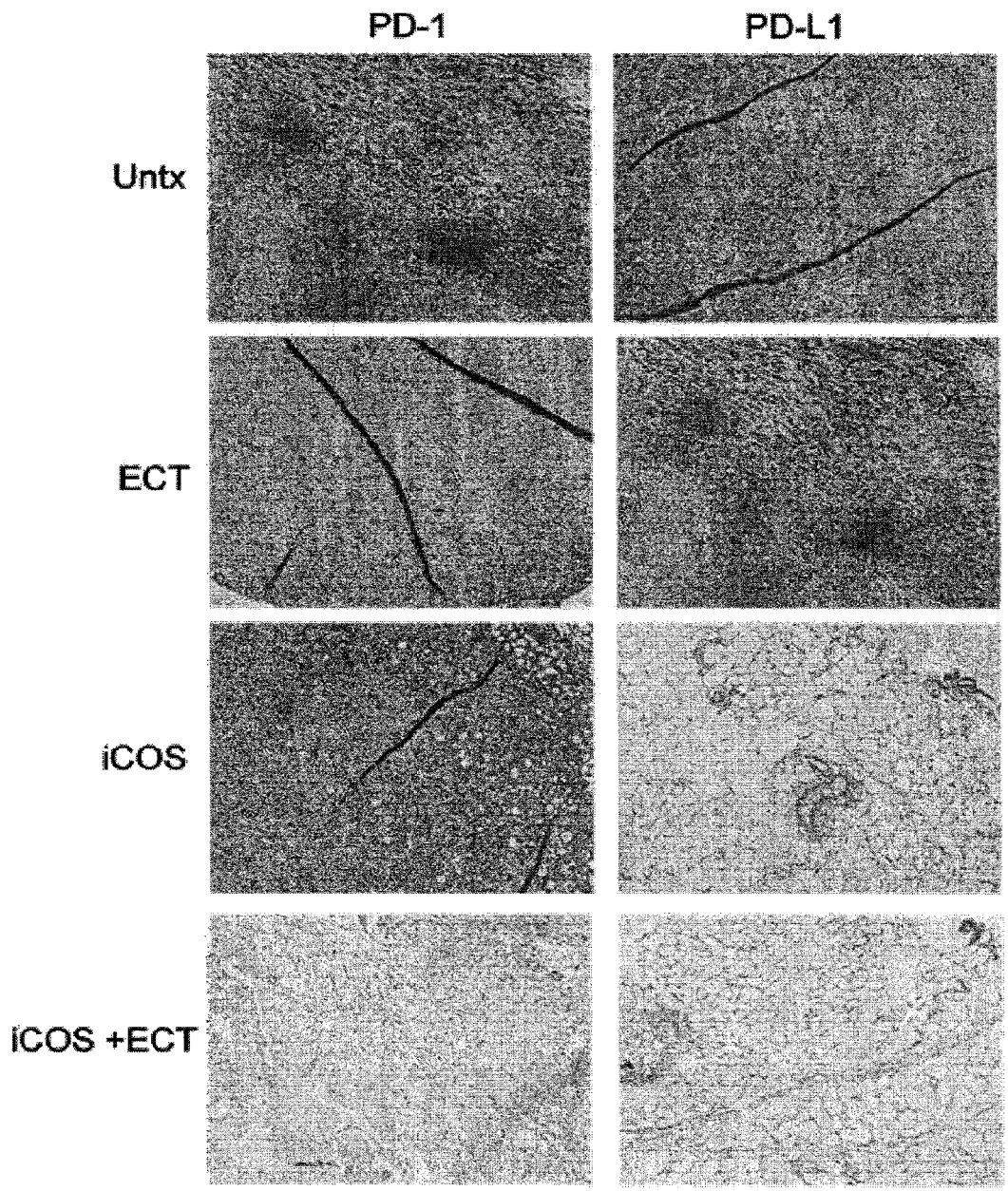

FIG. 6: Programmed Cell Death Receptor 1 (PD-1) and Programmed Cell Death Ligand (PD-L1) expression PD-1 and PD-L1 expression within tumour tissue.

Figure 7:
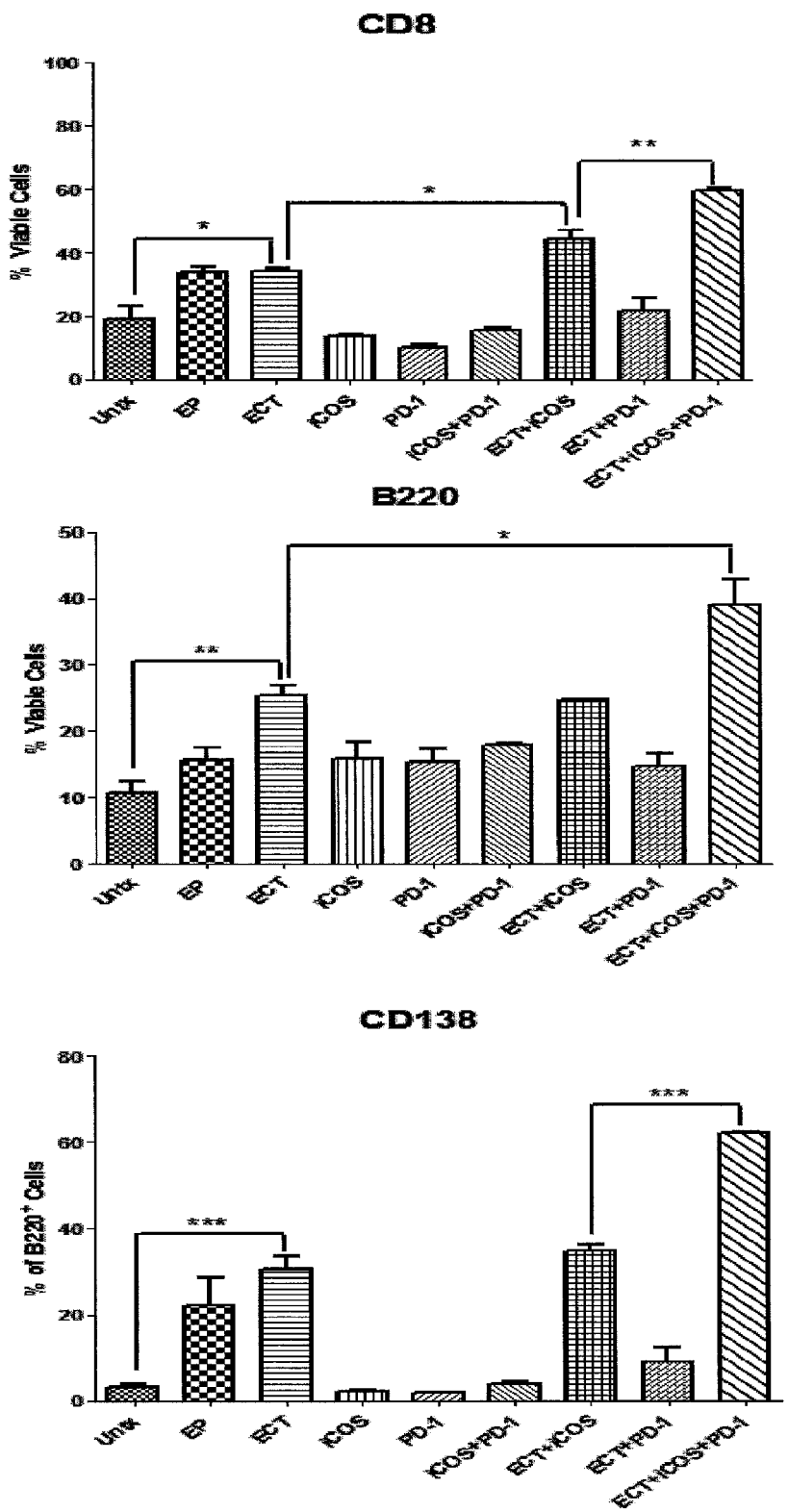

FIG. 7: Flow cytometry (1)

Flow cytometry analysis of excised tumour tissue.

Figure 8:
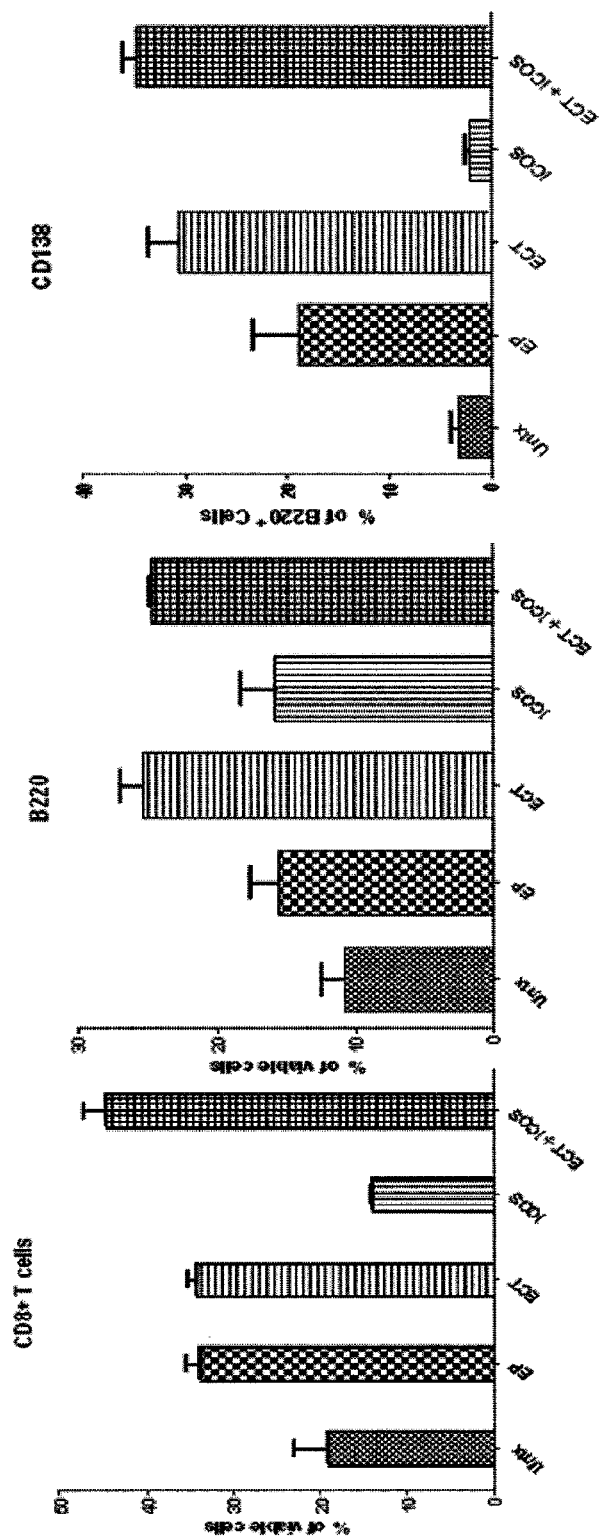

FIG. 8: Flow cytometry (2)

FIG. 8 presents a repeat of the flow cytometry data limited to the relevant iCOS groups: CD8+ T cells, B220, CD138.

Figure 9:
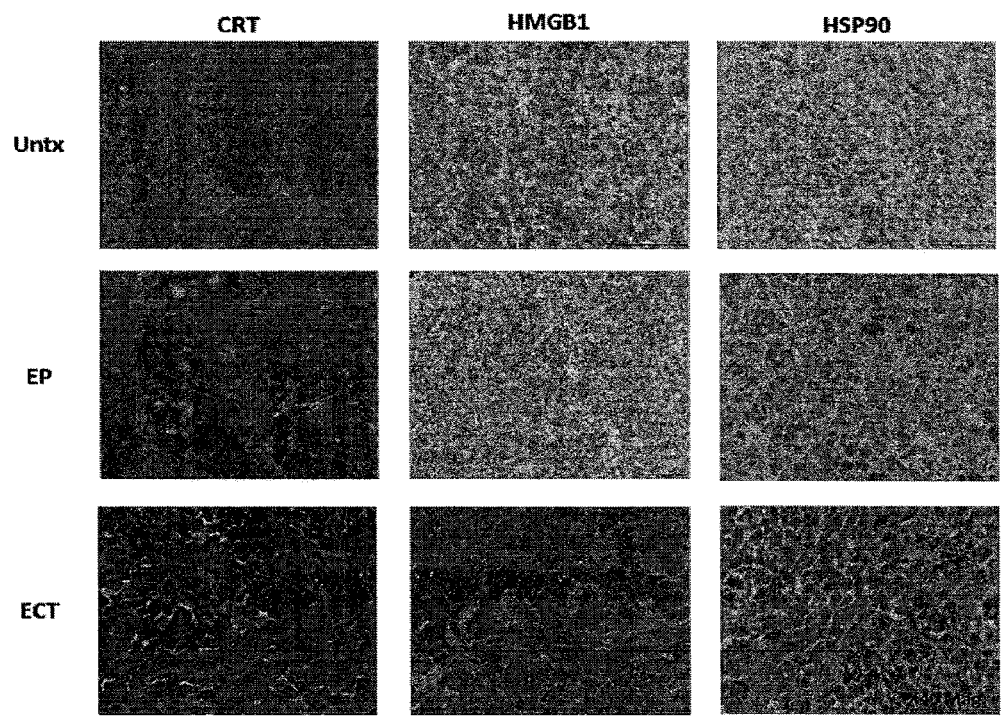

FIG. 9: Immunohistochemistry

Immunohistochemistry (IHC) staining for 3 main Damage Associated Molecular Proteins (DAMPs) in response to ECT treatment. Groups shown: Untreated (Untx), Electroporation (EP), Electrochemotherapy (ECT). Calreticulin (CRT), High Mobility Group Box Protein 1 (HMGB1) and Heat Shock Protein 90 (HSP90).

Figure 10A:
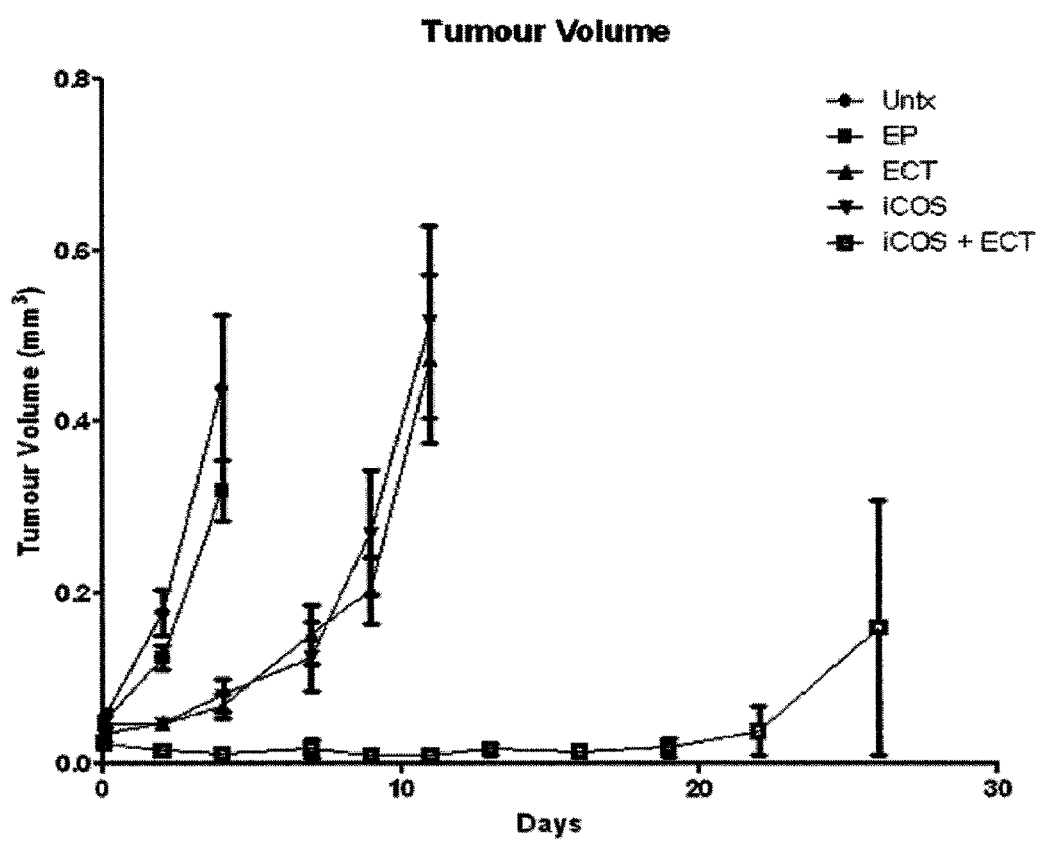
Figure 10B:
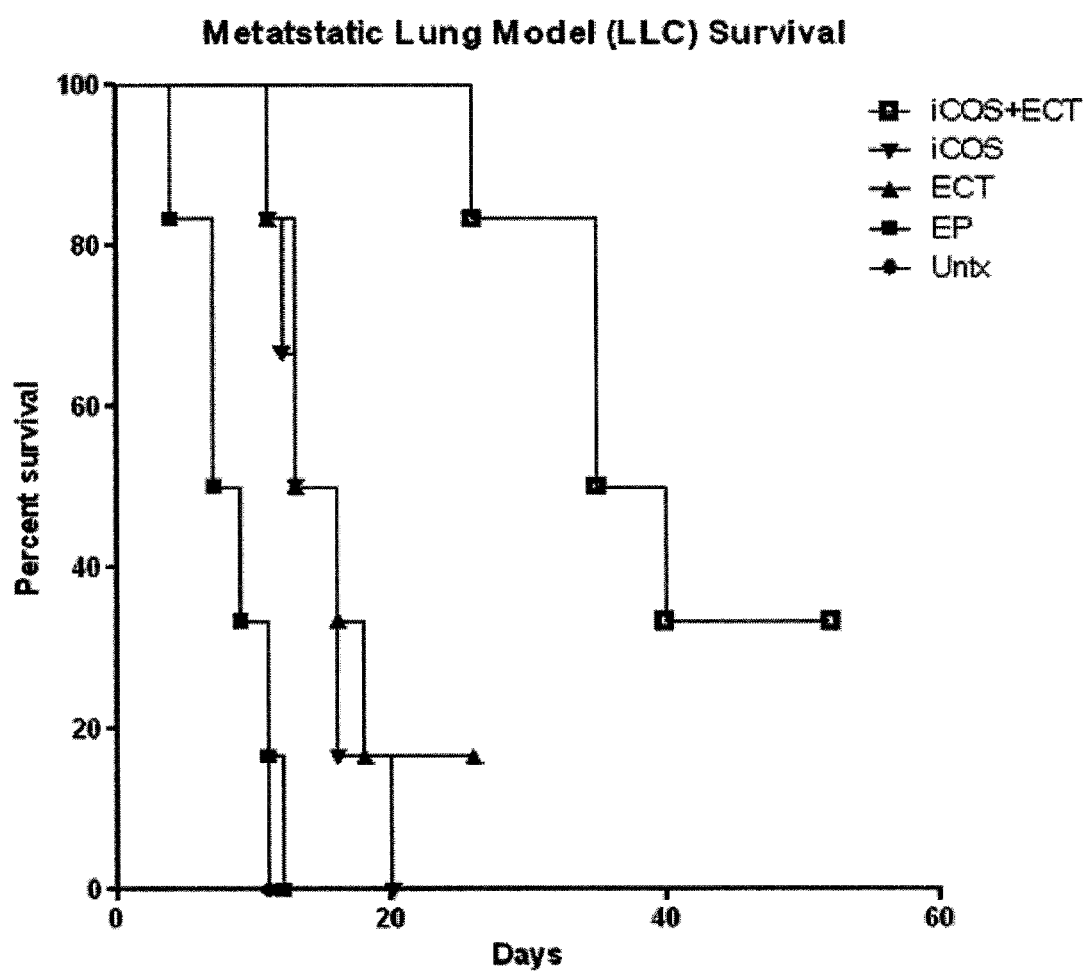

FIG. 10: Tumour growth and survival in metastatic lung cancer model (LLC) FIG. 10a—tumour volume; FIG. 10b—Survival.

SUMMARY OF ASPECTS OF THE INVENTION

In a first aspect the present invention provides a method for the treatment of cancer in a subject which comprises the steps of:
 (i) administering electroporation to a tumour in the subject; and
 (ii) administering a T or B-cell activating agent to the subject,
 wherein step (i) and (ii) may be performed in either order.

The method may further comprise the administration of calcium and/or a chemotherapeutic agent selected from a list comprising: alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinum coordination complexes such as cisplatin and carboplatin, bleomycin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

The chemotherapeutic agent may be cisplatin or bleomycin or alternatively another agent capable of inducing necrotic or apoptotic cell death after cell electroporation e.g. $CaCl_2$.

The T or B cell activating agent may be selected from a list comprising: inducible Cell co-stimulator (ICOS) agonist, lactoferrin, Iscador, CD27 agonist, CD40 agonist, BTLA antagonist, CD30 antagonist, Receptor Activator of Nuclear Factor κB (RANK) agonist, CD2 agonist, OX40 agonist, 4-1BB (CD137) agonist, phosphatidyserine antibodies, toll-like receptor (TLR) agonist, interleukin (IL)-2, interferon (IFN)-α, IFN-β, IFN-γ.

The T or B cell activating agent may be an ICOS agonist.

The method may involve the administration of a combination of T or B cell activating agents. The combination of T or B cell activating agents may be an ICOS agonist and IL-2.

The T or B cell activating agent may be administered systemically to the subject. The T or B cell activating agent may be administered by subcutaneous (SC), intraperitoneal (IP) or intravenous (IV) administration.

The T or B cell activating agent may be administered by intra-tumoural (IT) administration.

The T or B cell activating agent may be administered by pulse administration.

The electroporation may be administered prior to administration of the T or B cell activating agent.

The T or B cell activating agent may be administered up to 72 hours after the electroporation.

The interstitial pressure of the tumour may be lowered prior to or simultaneously to administration of the T or B cell activating agent. The interstitial pressure of the tumour may be lowered by a vacuum, a sonic wave or administration of an enzyme.

The T or B cell activating agent may be administered using a 'luer lock' administration.

The cancer may be a solid tumour. The solid tumour may be selected from a list comprising: gastrointestinal cancer; malignant melanoma; head and neck malignancies; squamous cell carcinoma; breast carcinoma; prostate cancer; lung cancer; glioblastoma; bladder cancer; cervical cancer; chordoma; kidney cancer; liver cancer; ovarian cancer; pancreatic cancer; sarcoma; thyroid cancer; testicular cancer; uterine cancer; urethral cancer; or vulvar cancer.

In a second aspect, the present invention provides a T or B cell activating agent for use in treating cancer according to the method the first aspect of the invention.

In a third aspect, the present invention provides a chemotherapeutic agent for use in treating cancer according to the method of the first aspect of the invention, in which the electroporation comprises administration of a chemotherapeutic agent.

In a fourth aspect, the present invention relates to the use of a T or B cell activating agent in the manufacture of a medicament for treating cancer according to the method of the first aspect of the invention.

In a fifth aspect, the present invention relates to the use of a chemotherapeutic agent in the manufacture of a medicament agent for treating cancer according to the method of the first aspect of the invention, in which the electroporation comprises administration of a chemotherapeutic agent.

In a sixth aspect, the present invention provides a kit which comprises a T or B cell activating agent and a chemotherapeutic agent for use in treating cancer according to the method of the first aspect, in which the electroporation comprises administration of a chemotherapeutic agent.

Thus, the present invention is based on a combination of electroporation and administration of a T or B-cell activating agent, which facilitates the activation of immune cells and the generation of an effective tumour antigen specific immune response. The combinatorial approach provided by the present invention results in increased survival levels compared to either chemotherapy or electroporation alone.

DETAILED DESCRIPTION

The present invention relates to a method for the treatment of cancer in a subject which comprises the steps of:
(i) administering electroporation to a tumour in the subject; and
(ii) administering a T or B-cell activating agent to the subject,
wherein step (i) and (ii) may be performed in either order.

As used herein, the term 'treatment'/'to treat' refers to performing the method on a subject in need of treatment in order to lessen, reduce or improve at least one symptom associated with the disease and/or to slow down, reduce or block the progression of the disease.

In the method of the present invention, the electroporation (step (i)) and T or B-cell therapy (step (ii)) may be performed in either order. That is, the method may comprise step (i), followed by step (ii) or step (ii), followed by step (i).

Electroporation

As used herein, the term 'electroporation' refers to the delivery of electrical fields/pulses to a solid tumour in a subject.

The standard treatment protocol for reversible electroporation involves the delivery of eight 100 μsec electric pulses (1000 v/cm, 8 square wave pulses, 100 μsec each) at a frequency of between 1 and 5 KHz.

Methods for the delivery of electrical pulses to solid tumours are well established in the art and numerous studies have demonstrated the successful delivery of electrical pulses to a variety of solid tumour types.

Irreversible Electroporation (IRE) is a phenomenon in which high electrical fields are delivered across cells in short, micro to millisecond pulses. These pulses create irreversible defects (pores) in the cell membrane lipid bilayer, causing cell death through loss of cell homeostasis. Non Thermal Irreversible Electroporation (NTIRE) operates to selectively affect only the cell membrane lipid bilayer and sparing all the other molecules in the volume of the treated tissue. NTIRE ablation efficacy is dependent on electric pulse parameters (number, length, frequency, magnitude and pulse shape). The electric field effect also depends on electrode design, cell morphology and its orientation, and extra cellular matrix properties herefore, NTIRE effect should therefore be evaluated separately for different tissues.

Electric pulses can be delivered by a variety of different electrodes. For example, plate electrodes with different gap between the plates may be used for treating small and superficial tumour nodules; needle electrodes may be used for the treatment of thicker and deeper-seated tumour nodules; whilst a hexagonal array of electrodes may be used for larger nodules.

Electroporation for solid tumours uses direct currents (all unipolar) with short and intense pulses (even though in vitro, time-decayed pulses can be used). The amplitude of the pulses depends on the tissues and on the shape and position of the electrodes, but, in vivo, the amplitude of the electric pulses has to be high enough to establish an electrical field of 400 V/cm in the area of tumour (8 pulses with duration of 100 microseconds). Pulses are generally delivered at a repetition frequency of 5000 Hz, resulting in a much less discomfort for the patient and in the shorter duration of treatment compared to earlier treatment procedures. For treatment of deep-seated tumours in relative vicinity of the heart, pulses are synchronized with absolute refractory period of each heartbeat to minimize the probability of interaction of pulses with the heart function.

The electroporation used in the method of the present invention may be performed with any electroporation system approved for clinical use.

T or B-Cell Activating Agent

As used herein, the term 'T or B-cell activating agent' refers to any entity which is capable of activating either a T-cell or B-cell.

The term 'activate'/'activating', as used herein, is synonymous with induce, enhance, upregulate and stimulate. As such, the T or B-cell activating agent may be any agent which is capable of stimulating or upregulating the activity of a T-cell or a B-cell. The terms T-cell activation and B-cell activation are well known in the art.

T-cells are divided into subsets. Cytolytic immune cells can be T cells or T lymphocytes which are a type of lymphocyte that play a central role in cell-mediated immunity. They can be distinguished from other lymphocytes, such as B cells and natural killer cells (NK cells), by the presence of a T-cell receptor (TCR) on the cell surface. There are various types of T cell, as summarised below.

Helper T helper cells (TH cells) assist other white blood cells in immunologic processes, including maturation of B cells into plasma cells and memory B cells, and activation of cytotoxic T cells and macrophages. TH cells express CD4 on their surface. TH cells become activated when they are presented with peptide antigens by MHC class II molecules on the surface of antigen presenting cells (APCs). These cells can differentiate into one of several subtypes, including TH1, TH2, TH3, TH17, Th9, or TFH, which secrete different cytokines to facilitate different types of immune responses. The activation of these TH subsets may be determined be the expression of specific cell surface markers and the expression and secretion of specific cytokines, as provided in the art.

Cytolytic T cells (TC cells, or CTLs) destroy virally infected cells and tumour cells, and are also implicated in transplant rejection. CTLs express the CD8 at their surface. These cells recognize their targets by binding to antigen associated with MHC class I, which is present on the surface of all nucleated cells. The activation of cytotoxic T cells is dependent on several simultaneous interactions between molecules expressed on the surface of the T cell and molecules on the surface of the antigen-presenting cell (APC), which provides the two signal model for TC cell activation. TC cell activation may be determined by the release of the cytotoxins perforin, granzymes, and granulysin. TC cell activation may also be determined by expression of express the surface protein FAS ligand (FasL)(Apo1L) (CD95L), and other markers provided in the art; in addition to the killing of target cells in in vitro cytotoxic killing assays.

The agent may be capable of activating a T-cell and/or a B-cell. The agent may be capable of activating a TC cell.

A non-exhaustive list of possible T or B-cell activating agents which may be used in the method of the present invention includes: inducible Cell co-stimulator (ICOS) agonist, lactoferrin, Iscador, a CD27 agonist, a CD40 agonist, a B- and T-lymphocyte attenuator (BTLA) antagonist, CD30 antagonist, Receptor Activator of Nuclear Factor κB (RANK) agonist, CD2 agonist, OX40 agonist, 4-1BB (CD137) agonist, phosphatidyserine antibodies, toll-like receptor (TLR) agonist, interleukin (IL)-2, interferon (IFN)-α, IFN-β and IFN-γ

The term 'agonist' is used herein to refer to an agent which is capable of inducing, stimulating or upregulating the activity of its target. As an illustration, an ICOS agonist is an agent which is capable of stimulating or upregulating the activity of ICOS, for example by inducing signalling through ICOS or increasing the level of signalling through ICOS.

Both small molecules and antibodies (in particular monoclonal antibodies) may act as agonists for a given target. Thus, in one embodiment, an agonist as described above is a monoclonal antibody. Examples of agonist monoclonal antibodies (such as anti-ICOS monoclonal antibodies having agonist properties) will be familiar to a person skilled in the art.

The term 'antagonist' is used herein to refer to an agent which is capable of blocking, preventing or downregulating the activity of its target. As an illustration, a BTLA antagonist is an agent is an agent which is capable of preventing or downregulating the activity of BTLA. For example, by preventing signalling through BTLA or reducing the level of signalling through BTLA.

Antagonists for a given target may also be small molecules or antibodies (in particular monoclonal antibodies). Thus, in one embodiment, an antagonist as described above is a monoclonal antibody. Examples of antagonist monoclonal antibodies will be familiar to a person skilled in the art.

A T or B-cell activating agent which is suitable for use in the method of the present invention may therefore by any agent which is capable of increasing the activation/activity of a T-cell or a B-cell compared to the level of activation/activity in the absence of the agent.

It is well known in the art that the activation of immune cells, including T-cells and B-cells, is controlled by a balance between positive activation signals (i.e. inducible Cell co-stimulator (ICOS) signalling) and negative repressive signals (i.e. B- and T-lymphocyte attenuator (BTLA) signalling). Dominance of positive activation signals leads to immune cell activation, whilst dominance of negative repressive signals prevents immune cell activation.

The T or B-cell activating agent for use in the method of the present invention may be an agent which activates a T-cell or a B-cell by stimulating/activating a positive activation signal (i.e. rather than inhibiting/downregulating a negative repressive signal).

A non-exhaustive list of such T or B-cell activating agents includes: ICOS agonist, lactoferrin, Iscador, CD27 agonist, RANK agonist, CD2 agonist, OX40 agonist, 4-1BB agonist, phosphatidyserine antibodies, toll-like receptor (TLR) agonist, interleukin (IL)-2, interferon (IFN)-α, IFN-β and IFN-γ.

In certain embodiments, the method of the present invention may comprise the administration of a combination of T or B-cell activating agents. For example, the method may comprise the administration of at least two, at least three or a plurality of T or B-cell activating agents. The method may comprise the administration of at least one T-cell activating agent and at least one B-cell activating agent. The method may comprise the administration of at least two T-cell activating agents. The method may comprise the administration of at least two B-cell activating agents.

The combination of T or B cell activating agents may be an ICOS agonist and IL-2.

Administration

The T or B-cell activating agent for use in the method of the present invention may be administered systemically to the subject.

For example the agent may be administered by intravenous (i.v), intraperitoneal (i.p), intra-arterial, intraventricular, intraepidural, oral or nasal administration.

The T or B-cell activating agent may be administered to the subject by intratumoural administration.

The therapeutically effective amount of one or more T or B-cell activating agents for use in the method of the present invention can be determined by the ordinarily-skilled artisan with consideration of individual differences in age, weight, and the condition of the subject. The agents are administered to a subject (e.g. a mammal, such as a human) in an effective amount, which is an amount that produces a desirable result in a treated subject (e.g. the slowing or remission of a cancer). Therapeutically effective amounts can be determined empirically by those of skill in the art.

The T or B-cell activating agent may be administered prior to, simultaneously to, or following the administration of the electroporation.

The T or B-cell activating agent may be administered up to 168, up to 120, up to 72, up to 48, up to 24, up to 12, up to 6, up to 4 or 2 hours prior to the administration of the electroporation.

The T or B-cell activating agent may be administered from less than two hours before to less than two hours following the administration of the electroporation. As used herein, this time range refers to the simultaneous administration of the T or B-cell activating agent and the electroporation.

The T or B-cell activating agent may be administered up to 168, up to 120, up to 72, up to 48, up to 24, up to 12, up to 6, up to 4 or 2 hours following the administration of the electroporation.

In certain embodiments, the T or B-cell activating agent may be administered by pulse administration. As such, the T or B-cell activating agent may be administered at several (i.e. more than one) time-points following the administration of the electroporation.

For example, the T or B-cell activating agent may be administered at least once, at least twice, up to a plurality of occasions following the electroporation. The T or B-cell activating agent may be administered at 6, 12, or 24 hour intervals, or up to several days and weeks apart, targeting the optimal period for immune cell antigen presentation facilitated by the electroporation treatment.

The T or B-cell activating agent may be administered simultaneously to the electroporation, followed by further administrations at 24 hours, 48 hours and 72 hours following electroporation. The T or B-cell activating agent may be administered simultaneously to the electroporation, followed by further administrations at 24 hours and 72 hours following electroporation.

The T or B-cell activating agent may be administered 24 hours, 48 hours and 72 hours following the electroporation.

The T or B-cell activating agent may be administered 24 hours and 72 hours following the electroporation.

The T or B-cell activating agent may be administered using a 'leur lock' administration. A 'leur lock' administration is a standardized system of small-scale fluid fittings used for making leak-free connections between a male-taper fitting and its mating female part on medical and laboratory instruments, including hypodermic syringe tips and needles or stopcocks and needles.

There are two varieties of Luer connections: Luer-Lock and Luer-Slip. Luer-Lock fittings are securely joined by means of a tabbed hub on the female fitting which screws into threads in a sleeve on the male fitting. Luer-Slip fittings simply conform to Luer taper dimensions and are pressed together and held by friction (they have no threads). Luer components are manufactured either from metal or plastic and are available from many companies worldwide.

Interstitial Pressure

In certain embodiments, the interstitial pressure of the tumour is lowered prior to administration of the T or B-cell activating agent.

The 'interstitial pressure of the tumour' refers to hydrostatic pressure in the interstitial fluid which surrounds the tumour cells. Tumours can have high positive interstitial pressure throughout the interior, while pressure in the outermost areas remains at close to normal physiological (marginally negative) levels. This negatively impacts on the flow by convection of molecules from the capillaries around the tumour into the tumour interstitial spaces.

A non-exhaustive, illustrative list of tumours which have been shown to have high interstitial pressure includes; renal cell carcinoma, cervical carcinoma, colorectal liver metastases, head and neck carcinoma, breast carcinoma, metastatic carcinoma and lung carcinoma.

The interstitial pressure of a tumour may be lowered using methods known in the art. For example, the interstitial pressure may be lowered using a vacuum, an enzyme or sonic waves.

Vacuum—The use of a vacuum reduces the liquid stress. It creates an artificial lymphatic drainage system which reduces fluid/liquid stress and causes negative pressure to be formed.

Enzyme—The use of enzymes reduces the solid stress: it is not a fluid based approach. The microenvironment in tumors is different than that of normal tissue. There is an increased number of fibroblasts in tumor stroma that stimulates the expansion of ECM and increase the matrix tension. This is due to the synthesis of abnormally large amount of collagen fibers, hyaluronan, GAGs, proteoglycans, and proteolytic enzymes and its inhibitors. Examples of enzymes include collagen degrading enzymes and Hyaluronan.

Sonic wave approaches, such as ultrasound—The soundwaves are transmitted as an alternation series of compressions (zones of high pressure) and rarefractions (zones of low pressure). Ultrasound reduces tumour interstitial pressure due to mechanical (cavitation, radiation pressure) and thermal effects. Thermal effects cause damage to tumor cells and ECM which increase the interstitial hydraulic conductivity, reduce matrix tension and enhance tumor blood flow.

Sonic waves produced by medical ultrasound devices may also be used to lower the interstitial pressure in a tumour. Ultrasound exposures may be provided using focused transducers which allow ultrasound waves to be focused onto very small volumes, which greatly increases their intensity—high intensity focused ultrasound (HIFU). Focused beams are created using spherically-curved transducers, allowing energy to be deposited deep inside the body.

Electrochemotherapy

The method of the present invention may further comprise administration of calcium and/or a chemotherapeutic agent to a subject in need of treatment.

The administration of a chemotherapeutic agent in combination with electroporation is termed 'electrochemotherapy' (ECT). ECT allows the delivery of non-permeant drugs to the cell interior. It is based on the local application of short and intense electric pulses that transiently permeabilize the cell membrane, thus allowing transport of molecules otherwise not permitted by the membrane. With the delivery of the electric pulses, cells are subjected to an electric field that causes the formation of nanoscale defects on the cell membrane, which alter the permeability of the membrane. At this stage and for some time after pulses are delivered, molecules of the cytotoxic agents can freely diffuse into the cytoplasm and exert their cytotoxic effect. Multiple positioning of the electrodes, and subsequent pulse delivery, can be performed during a session to treat the whole lesion, provided that drug concentration is sufficient. Treatment can be repeated over the course of weeks or months to achieve regression of large lesions.

A chemotherapeutic agent contemplated includes, without limitation, alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinium coordination complexes such as cisplatin and carboplatin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

The chemotherapeutic agent may be cisplatin or bleomycin.

Alternatively $CaCl_2$ may be used to induce tumour necrosis post electroporation.

Cisplatin is also known as cisplatinum, or cis-diamminedichloroplatinum (CDDP). It was the first member of a class of platinum-containing anti-cancer drugs, which now also includes carboplatin and oxaliplatin. These platinum complexes react in vivo, binding to and causing crosslinking of DNA, which ultimately triggers apoptosis (programmed cell death).

Bleomycin is a glycopeptide antibiotic produced by the bacterium *Streptomyces verticillus*. Bleomycin refers to a family of structurally related compounds. The chemotherapeutical forms are primarily bleomycin A2 and B2, which function by inducing breaks in DNA.

The chemotherapeutic agent may be administered to the subject via a systemic administration method. For example, the agent may be administered by intravenous (i.v), intraperitoneal (i.p), intra-arterial, intraventricular, intraepidural, oral or nasal administration.

The chemotherapeutic agent may be administered to the subject by intratumoural.

The therapeutically effective amount of one or more chemotherapeutic agents for use in the method of the present invention can be determined by the ordinarily-skilled artisan with consideration of individual differences in age, weight, and the condition of the mammal. The agents are administered to a subject (e.g. a mammal, such as a human) in an effective amount, which is an amount that produces a desirable result in a treated subject (e.g. the slowing or remission of a cancer). Therapeutically effective amounts can be determined empirically by those of skill in the art.

The timing of the administration of the chemotherapeutic agent with respect to the electroporation may be performed according to the methods known in the art.

For example, the chemotherapeutic agent may be administered prior to, simultaneously to, or post the administration of the electroporation.

The chemotherapeutic agent may be administered up to 168, up to 120, up to 72, up to 48, up to 24, up to 12, up to 6, up to 4 or 2 hours prior to the administration of the electroporation.

The chemotherapeutic agent may be administered from less than two hours before to less than two hours following the administration of the electroporation. As used herein, this time range refers to the simultaneous administration of the chemotherapeutic agent and the electroporation.

The chemotherapeutic agent may be administered up to 168, up to 120, up to 72, up to 48, up to 24, up to 12, up to 6, up to 4 or 2 hours post the administration of the electroporation.

Cancer

The method of the present invention is used to treat cancer.

The method may be used to treat a solid tumour. The term 'solid tumour' is used herein to refer to a malignant neoplasm. Thus it includes all cancers, other than leukaemia.

A non-exhaustive, illustrative list of solid tumours which may be treated by the method of the present invention includes; gastrointestinal cancer; malignant melanoma; head and neck malignancies; squamous cell carcinoma; breast carcinoma; prostate cancer; lung cancer; glioblastoma; bladder cancer; cervical cancer; chordoma; kidney cancer; liver cancer; ovarian cancer; pancreatic cancer; sarcoma; thyroid cancer; testicular cancer; uterine cancer; urethral cancer; and vulvar cancer.

Use

The present invention also provides a T or B-cell activating agent, as defined herein, for use in treating cancer according to the method of the first aspect of the invention.

The present invention further relates to the use of a T or B-cell activating agent, as defined herein, in the manufacture of a medicament for treating cancer according to the method of the first aspect of the invention.

Kit

The present invention also provides a kit which comprises a T or B-cell activating agent and a chemotherapeutic agent, as defined herein, for use in treating cancer according to the method of the first aspect of the invention, in which the electroporation comprises administration of the chemotherapeutic agent.

The invention will now be further described by way of Examples, which are meant to serve to assist one of ordinary skill in the art in carrying out the invention and are not intended in any way to limit the scope of the invention.

EXAMPLES

Example 1

Effect of ECT Combined with ICOS on Tumour Growth in CT26 Model

Figure 1:
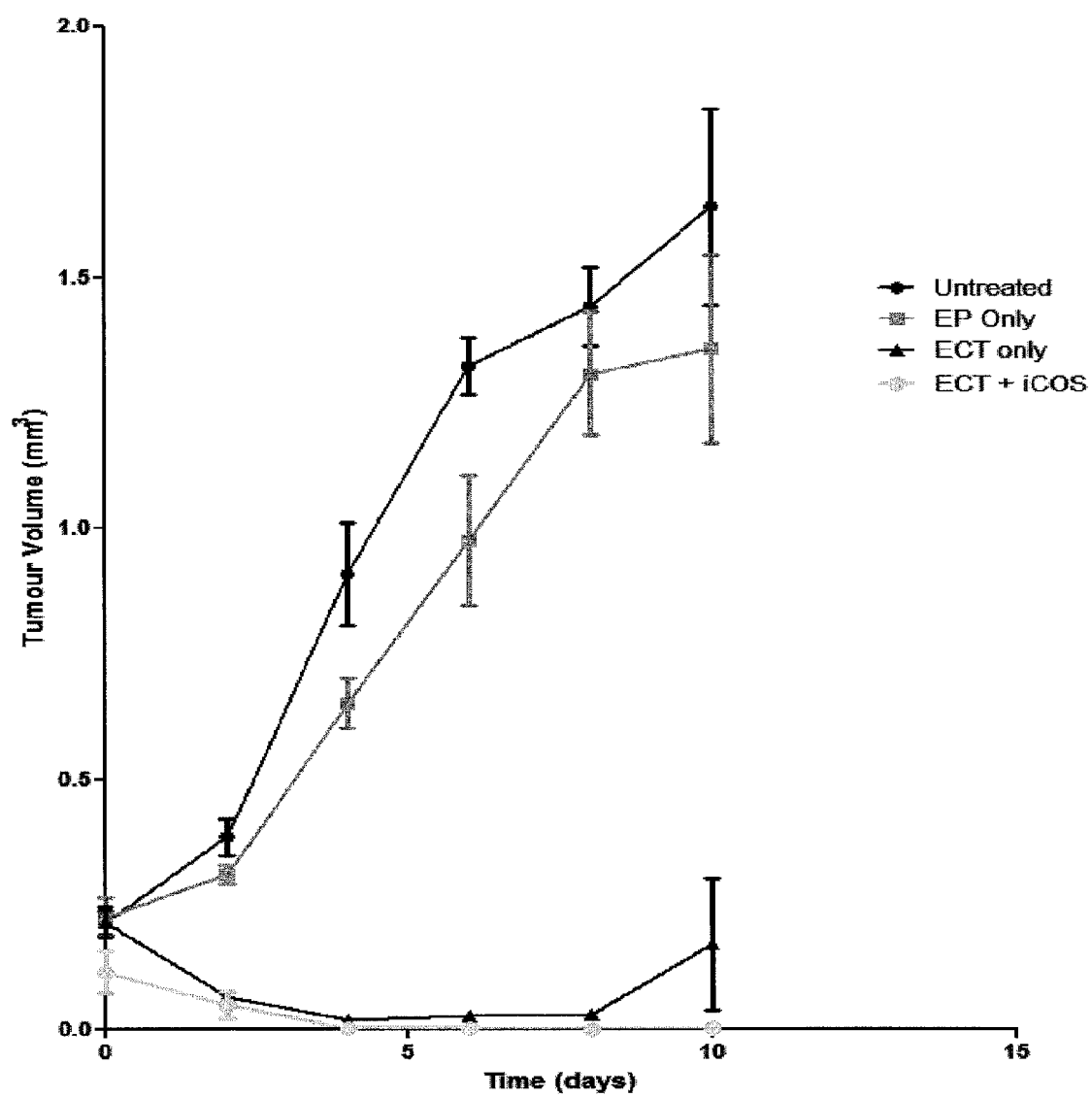
FIG. 1: Growth curve of ECT combined with ICOS in CT26 model

Balb/C mice were subcutaneously injected with $1\times10^6$ CT26 cells. When tumours reached an approximate size of 100 mm$^3$ they were treated with electroporation only, electrochemotherapy only (ECT), electrochemotherapy combined with ICOS or untreated (FIG. 1).

Example 2

Effect of ECT Combined with ICOS on Survival in CT26 Model

Representative Kaplan-Meier survival curve of CT26 treated tumours was measured. Only mice treated with ICOS/ECT combination survived as 40% of mice survived and were still alive at approx. 200 days. All other groups were sacrificed by day 38 (FIG. 2)

Example 3

Effect of ECT Combined with ICOS on Tumour Growth in B16F10 Model

C57BL/6J mice were subcutaneously injected with $2\times10^5$ B16F10 cells in the flank. When the tumours grew to an approximate size of 100 mm$^3$ they were treated with electroporation only, electrochemotherapy only, electrochemotherapy combined with ICOS, ICOS only or untreated (FIG. 3).

Example 4

Effect of ECT Combined with ICOS on Survival in B16F10 Model

Representative Kaplan-Meier survival curve of B16F10 treated tumours was measured. Mice treated with ICOS/ECT combination survived to 48 days. All other groups were sacrificed by day 25 (FIG. 4).

Example 5

Effect of ECT Combined with ICOS on Lung Tumour Size

The effect of ECT combined with ICOS was examined in a metastatic lung cancer model. Lung weight is a physical indicator for the presence of lung metastases. Both the untreated (Untx) and electroporation (EP) groups had lung weights almost four times that of the healthy control, indicating a high metastases burden in the lungs. Lung weights in the Electrochemotherapy (ECT) and iCOS groups showed a slight increase compared to the healthy control, but the combinational group (iCOS plus ECT) exhibited a lung weight comparable to that of the healthy control. The significance of this is that only the primary tumours of the animals were treated but the treatment was also successful against secondary/distal tumours (FIG. 5).

Example 6

Cell Histology

Programmed Cell Death Receptor 1 (PD-1) and Programmed Cell Death Ligand (PD-L1) are molecules belonging to the B7 superfamily, which mediates immune cell responses towards cancer cells. When PD-1 and PD-L1 bind within the tumour microenvironment, it causes T cell energy by interfering with key immune signalling and so both PD-1 and PD-L1 expression within tumour tissue are negative prognostic markers. High levels of both staining were shown in the Untx and ECT groups and even the PD-1 receptor staining was quite high for the iCOS only group. However there was a dramatic decrease in expression of both after treatment with iCOS plus ECT. If PD-1 and PD-L1 are not expressed then they can no longer cause T cell energy and a more prolonged immune response can be achieved (FIG. 6).

Example 7

Flow Cytometry Analysis

Flow cytometry analysis was carried out on excised tumour tissue. This analysis showed significant increases in the following immune cell populations in response to the ECT and immunotherapy combinations: CD8+ T cells (key immune cells that target and kill tumour cells), B220+ B cells (responsible for immune cell signalling), and CD138+ memory B cells (B cells that produce antibodies specific to the tumour, allowing for the generation of immune memory against the tumour) (FIGS. 7-8).

Example 8

Immunohistochemistry

Immunohistochemistry (IHC) staining was performed for three main Damage Associated Molecular Proteins (DAMPs), in response to ECT treatment. DAMPs play key roles in immune activation when expressed extracellularly by interacting with Antigen Presenting Cells (APCs). ECT caused dramatic increases in the levels of Calreticulin (CRT), High Mobility Group Box Protein 1 (HMGB1) and Heat Shock Protein 90 (HSP90). This indicates that ECT alone is sufficient to prime the immune system and generate a weak but positive immune response, that can then be potentiated with combination immunotherapy (FIG. 9).

Example 9

Metastatic Lung Cancer Model

Tumour growth and animal survival were analysed in the metastatic lung cancer model. Treatment with combination immunotherapy (iCOS plus ECT) produced significant inhibition in tumour growth and significant increases in animal survival (40-60% cures across multiple experiments and tumour models) (FIG. 10).

Materials and Methods

Cell Tissue Culture

Tumour cell lines CT26 and B16F10 were obtained from the American Type Cell Collection (Manassas, Va.). The murine colon adenocarcinoma, CT26 was cultured with Dulbecco's modified Eagle's media (Sigma) supplemented with 10% v/v fetal calf serum, 300 μg/ml L-glutamine. The mouse melanoma B16F10 cell line was cultured in RPMI-1640 (Sigma) supplemented with 10% v/v fetal calf serum and 300 μg/ml L-glutamine. Cells were maintained in logarithmic phase growth at 37° C. in a humidified atmosphere supplemented with 5% CO2.

Animals and Tumour Induction

Female Balb/c and C57BL/6J (6-8 weeks) were obtained from Harlan Laboratories (Oxfordshire, England). For routine tumour induction, $1 \times 10^6$ CT26 and $2 \times 10^5$ B16F10 tumour cells suspended in 200 μl of serum free DMEM were injected subcutaneously into the flank of the female Balb/C or C57 BL/6J. Following tumour establishment, tumours were allowed to grow and develop and were monitored by alternate day measurements in two dimensions using vernier callipers. Tumour volume was calculated according to the formula $V=ab^2\pi/6$, where a is the longest diameter of the tumour and b is the longest diameter perpendicular to diameter a. From these volumes, tumour growth curves were constructed. Mice euthanized when the tumour diameter was between 1.7 cm$^3$.

Ethics Statement

All murine husbandry and experimental procedures were approved by the University College Cork Animal Experimentation Ethics Committee and carried out under licenses issued by the Department of Health, Ireland as directed by the Cruelty to Animals Act Ireland and EU Statutory Instructions.

In Vivo Electroporation

Once tumours reached a size of 0.3 cm×0.3 cm, electrochemotherapy was administered using an established, standard operation procedure. Procedures were performed under local anaesthesia, a combination of ketamine (2-10 mg/kg) and Xylazine (0.05-0.1 mg/kg) in 100 uL of sterile PBS, was administered via intra-peritoneal injection. The intra-tumoural dose of Cisplatin was set at 5 mg/kg in 200 ul sterile PBS and was administered pre electroporation. Electric pulses were generated by the Cliniporator (IGEA, Carpi, Italy) (8 square wave pulses 1000 V/cm for 100 μs at 5 kHz) and were delivered into the tumours using 3 pairs of linear needle electrodes.

Chemotherapeutic Drugs

Cisplatin: is a chemotherapy drug. It was the first member of a class of platinum-containing anti-cancer drugs, which now also includes carboplatin and oxaliplatin. These platinum complexes react in vivo, binding to and causing cross-linking of DNA, which ultimately triggers apoptosis.

Antibody

ICOS antibody: A member of the costimulatory molecule family, inducible costimulator (ICOS), is expressed on activated T or B cells and plays a critical role in their primary activation and cytokine production. The following anti-ICOS monoclonal antibodies were employed: Clone C398.4A, Biolegend; Clone 27A12, BioXCell.

Treatment Schedule

Day 0 ECT, Day 3: ICOS administration, Day 6: ICOS administration Day 9: ICOS administration.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in immunology, cardiac biology or related fields are intended to be within the scope of the following claims.

The invention claimed is:

1. A method for the treatment of cancer in a subject which comprises the steps of:
    (i) administering electroporation to a tumour in the subject; and
    (ii) administering an inducible Cell co-stimulator (ICOS) agonist to the subject,
    wherein step (i) and (ii) may be performed in either order.

2. A method according to claim 1 wherein step (i) further comprises administration of calcium.

3. A method according to claim 1 wherein step (i) further comprises administration of a chemotherapeutic agent selected from a list comprising: alkylating agents, nitrosoureas, ethylenimines/methylmelamine, alkyl sulfonates, antimetabolites, pyrimidine analogs, epipodophylotoxins, enzymes such as L-asparaginase; biological response modifiers such as IFNα, IL-2, G-CSF and GM-CSF; platinium coordination complexes such as cisplatin and carboplatin, bleomycin, anthracenediones, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteriod antagonists such as prednisone and equivalents, dexamethasone and aminoglutethimide; progestin such as hydroxyprogesterone caproate, medroxyprogesterone acetate and megestrol acetate; estrogen such as diethylstillbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

4. A method according to claim 3 wherein the chemotherapeutic agent is selected from a list comprising: cisplatin or bleomycin.

5. A method according to claim 1 in which the ICOS agonist is administered systemically to the subject.

6. A method according to claim 5 in which the ICOS agonist is administered by subcutaneous (SC), intraperitoneal (IP) or intravenous (IV) administration.

7. A method according to claim 1 in which the ICOS agonist is administered by intra-tumoural (IT) administration.

8. A method according to claim 1 wherein the electroporation and the ICOS agonist are administered by pulse administration.

9. A method according to claim 1 wherein the electroporation is administered prior to administration of the ICOS agonist.

10. A method according to claim 9 in which the ICOS agonist is administered up to 72 hours after the electroporation.

11. A method according to claim 1 wherein the interstitial pressure of the tumour is lowered prior or simultaneously to administration of the ICOS agonist.

12. A method according to claim 11 wherein the interstitial pressure of the tumour is lowered by a vacuum, a sonic wave or administration of an enzyme.

13. A method according to claim 1 wherein the ICOS agonist is administered using a 'luer lock' administration.

14. A method according to claim 1 wherein the cancer is a solid tumour.

15. A method according to claim 14 wherein the solid tumour is selected from a list comprising: gastrointestinal cancer; malignant melanoma; head and neck malignancies; squamous cell carcinoma; breast carcinoma; prostate cancer; lung cancer; glioblastoma; bladder cancer; cervical cancer; chordoma; kidney cancer; liver cancer; ovarian cancer; pancreatic cancer; sarcoma; thyroid cancer; testicular cancer; uterine cancer; urethral cancer; or vulvar cancer.

* * * * *